(12) United States Patent
Konagayoshi et al.

(10) Patent No.: US 10,800,672 B2
(45) Date of Patent: Oct. 13, 2020

(54) FLUID STERILIZATION APPARATUS

(71) Applicant: NIKKISO CO., LTD., Tokyo (JP)

(72) Inventors: Hidenori Konagayoshi, Ishikawa (JP); Nobuhiro Torii, Ishikawa (JP); Tetsumi Ochi, Ishikawa (JP); Hiroki Kiuchi, Ishikawa (JP)

(73) Assignee: Nikkiso Co., Ltd, Tokyo (JP)

( * ) Notice: Subject to any disclaimer, the term of this patent is extended or adjusted under 35 U.S.C. 154(b) by 0 days.

(21) Appl. No.: 15/933,939

(22) Filed: Mar. 23, 2018

(65) Prior Publication Data

US 2018/0208486 A1 Jul. 26, 2018

Related U.S. Application Data

(63) Continuation of application No. PCT/JP2016/077435, filed on Sep. 16, 2016.

(30) Foreign Application Priority Data

Sep. 25, 2015 (JP) .................. 2015-188825

(51) Int. Cl.
*C02F 1/32* (2006.01)
*A61L 2/10* (2006.01)
(Continued)

(52) U.S. Cl.
CPC ................ *C02F 1/325* (2013.01); *A61L 2/10* (2013.01); *A61L 2/24* (2013.01); *B01J 19/123* (2013.01);
(Continued)

(58) Field of Classification Search
CPC .... C02F 1/325; C02F 1/32; C02F 2201/3223; C02F 2201/3228; C02F 2201/3221;
(Continued)

(56) References Cited

U.S. PATENT DOCUMENTS

2003/0030011 A1* 2/2003 Brown .................. A61L 2/0011
250/455.11
2004/0061069 A1 4/2004 Schalble et al.
(Continued)

FOREIGN PATENT DOCUMENTS

AU 2015210393 A1 9/2015
CN 102448891 A 5/2012
(Continued)

OTHER PUBLICATIONS

An International Preliminary Report on Patentability issued in corresponding Application No. PCT/JP2016/077435 is attached.
(Continued)

*Primary Examiner* — Xiuyu Tai
(74) *Attorney, Agent, or Firm* — Muncy, Geissler, Olds & Lowe, P.C.

(57) ABSTRACT

A sterilization apparatus is provided with: a light source, which has a semiconductor light-emitting element that emits ultraviolet light; a housing, which forms a flow passage through which a fluid subject to sterilization passes; a light receiving unit, which receives a portion of the ultraviolet light emitted from the light source and detects the amount of ultraviolet light that has been received; and a control unit, which controls the output of the semiconductor light-emitting element based on information regarding the amount of ultraviolet light acquired from the light receiving unit. The housing has an incidence portion on which ultraviolet light becomes incident and a reflection portion, which reflects the ultraviolet light at the inner surface thereof. The light receiving unit is provided at a position where the light receiving unit can receive the portion of ultraviolet light that has been transmitted through the reflection portion.

7 Claims, 3 Drawing Sheets

(51) Int. Cl.
*A61L 2/24* (2006.01)
*B01J 19/12* (2006.01)

(52) U.S. Cl.
CPC ........... *C02F 1/32* (2013.01); *A61L 2202/122* (2013.01); *A61L 2202/14* (2013.01); *B01J 2219/0877* (2013.01); *C02F 2201/3223* (2013.01); *C02F 2201/3228* (2013.01)

(58) Field of Classification Search
CPC .......... C02F 2209/006; C02F 2201/326; C02F 2201/3225; C02F 2201/3222; C02F 2201/3227; A61L 2/10; A61L 2/24; B01J 19/123; B01J 2219/0877
See application file for complete search history.

(56) References Cited

U.S. PATENT DOCUMENTS

| | | |
|---|---|---|
| 2007/0012883 A1 | 1/2007 | Lam |
| 2009/0155136 A1 | 6/2009 | Cooper et al. |
| 2010/0084349 A1* | 4/2010 | Levy ................. C02F 1/325 210/745 |
| 2015/0060692 A1* | 3/2015 | Chen ................. C02F 1/325 250/435 |

FOREIGN PATENT DOCUMENTS

| | | |
|---|---|---|
| JP | 2004066045 A | 3/2004 |
| JP | 2005227241 A | 8/2005 |
| JP | 2007502200 A | 2/2007 |
| JP | 2011509169 A | 3/2011 |
| JP | 2014002015 A | 1/2014 |
| JP | 2014087544 A | 5/2014 |
| KR | 2010-0137412 A | 12/2010 |
| WO | WO99/57528 | 11/1999 |
| WO | WO-2005/011753 A1 | 2/2005 |
| WO | WO2013/140899 A1 | 9/2013 |
| WO | WO 2018/037939 A1 | 3/2018 |

OTHER PUBLICATIONS

A Written Opinion dated Oct. 24, 2017 in corresponding Application No. PCT/JP2016/077435 is attached.
A Written Opinion dated Dec. 20, 2016 in corresponding Application No. PCT/JP2016/077435 is attached.
Japanese Office Action in application No. 2015-188825 dated Dec. 11, 2018, is attached and its English translation; pp. 1-6.
Korean Office based on corresponding Application No. 2016800554780. 5, dated Oct. 31, 2019.
Chinese Notice of Reason(s) for Refusal based on corresponding Application No. 10-2018-7011367, dated Aug. 29, 2019.

* cited by examiner

FLUID STERILIZATION APPARATUS

RELATED APPLICATION

The present application is a continuation application of International Application No. PCT/JP2016/077435, filed Sep. 16, 2016, which claims priority to Japanese Patent Application No. 2015-188825, filed Sep. 25, 2015. The entire contents of these applications are incorporated herein by reference.

BACKGROUND OF THE INVENTION

1. Field of the Invention

The present invention relates to a fluid sterilization apparatus.

2. Description of the Related Art

In the related art, sterilization by ultraviolet light irradiation has been carried out in various fields. For example, a sterilization apparatus has been devised that sterilizes a fluid such as water (see Japanese Patent Application Publication No. 2014-87544). As a light source used for an ultraviolet sterilization apparatus, a mercury lamp is known that radiates light having a wavelength of 253.7 nm that is produced by an electric discharge in low-pressure mercury vapor.

Such an ultraviolet light source consumes large power and produces a large amount of heat, and the light source itself is large. Therefore, in recent years, an ultraviolet sterilization apparatus has been developed in which an ultraviolet light emitting diode that has a longer life and consumes less power compared to a mercury lamp is used as its light source. Further, since the output of an ultraviolet light emitting diode is gradually lowered with the use of the diode, a technology has been devised that detects the amount of ultraviolet light by a light receiving element and adjusts a driving signal based on information regarding the amount of ultraviolet light that has been detected so that the amount of ultraviolet light radiation of the light emitting diode is at a desired value (see Japanese Patent Application Publication No. 2005-227241).

If ultraviolet light that has entered a space through which a fluid passes can keep irradiating the fluid while repeating reflection inside the space, the number and output of ultraviolet light sources can be lowered. Meanwhile, it is necessary to detect, by some kind of method, a portion of ultraviolet light emitted from an ultraviolet light source in order to keep the output of the ultraviolet light source constant.

SUMMARY OF THE INVENTION

In this background, a purpose of the present invention is to provide a technology for efficient sterilization and stabilization of the output of an ultraviolet light source.

A fluid sterilization apparatus according to one embodiment of the present invention is provided with: a light source that has a semiconductor light-emitting element that emits ultraviolet light; a housing that forms a flow passage through which a fluid subject to sterilization passes; a light receiving unit that receives a portion of the ultraviolet light emitted from the light source and detects the amount of ultraviolet light that has been received; and a control unit that controls the output of the semiconductor light-emitting element based on information regarding the amount of ultraviolet light acquired from the light receiving unit. The housing has an incidence portion on which ultraviolet light becomes incident and a reflection portion that reflects the ultraviolet light at the inner surface thereof. The reflection portion is formed of a material that transmits a portion of ultraviolet light, and the light receiving unit is provided at a position where the light receiving unit can receive the portion of ultraviolet light that has been transmitted through the reflection portion.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which.

DETAILED DESCRIPTION OF THE INVENTION

Figure 1:
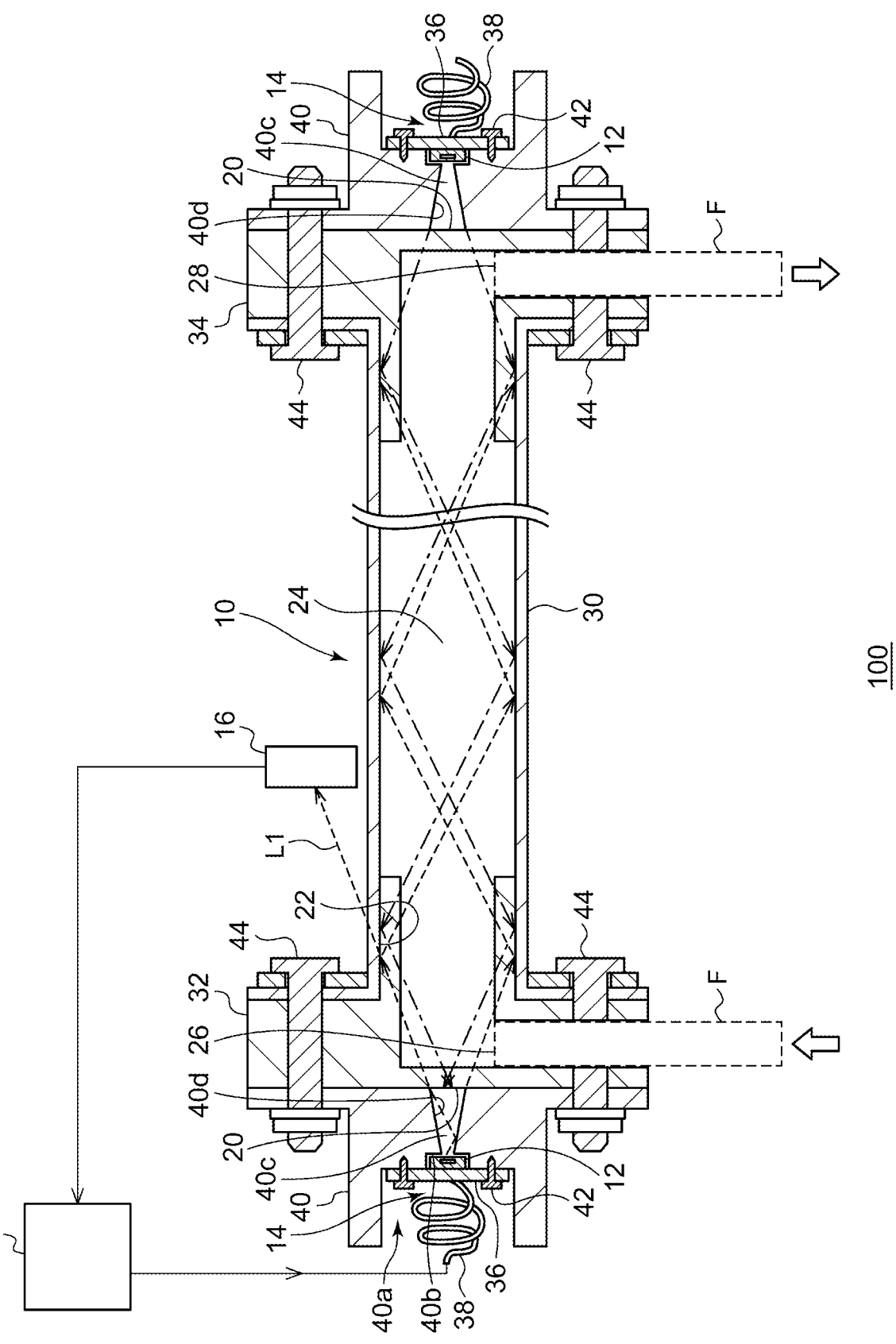
FIG. 1 is a schematic diagram showing a schematic configuration of a sterilization apparatus according to a present embodiment.

A fluid sterilization apparatus according to one embodiment of the present invention is provided with: a light source that has a semiconductor light-emitting element that emits ultraviolet light; a housing that forms a flow passage through which a fluid subject to sterilization passes; a light receiving unit that receives a portion of the ultraviolet light emitted from the light source and detects the amount of ultraviolet light that has been received; and a control unit that controls the output of the semiconductor light-emitting element based on information regarding the amount of ultraviolet light acquired from the light receiving unit. The housing has an incidence portion on which ultraviolet light becomes incident and a reflection portion that reflects the ultraviolet light at the inner surface thereof. The reflection portion is formed of a material that transmits a portion of ultraviolet light, and the light receiving unit is provided at a position where the light receiving unit can receive the portion of ultraviolet light that has been transmitted through the reflection portion.

According to this embodiment, ultraviolet light that is detected by the light receiving unit is a portion of ultraviolet light that has been transmitted through the reflection portion. Since ultraviolet light that has been transmitted through the reflection portion does not contribute to the sterilization, detecting the amount of light by the light receiving unit by using such ultraviolet light prevents the amount of ultraviolet light used for the sterilization from being reduced. Further, by controlling the output of the semiconductor light-emitting element based on information regarding the amount of ultraviolet light acquired by the light receiving unit, the output of the light source can be stabilized.

The light receiving unit may be arranged in a region opposite to the incidence portion across the reflection portion. This allows the light receiving unit to be provided outside the housing.

The reflection portion may be formed of a material whose diffuse reflectance for ultraviolet light having a wavelength of 285 nm is in a range of 78.5 to 95.4 percent and whose diffuse transmittance for ultraviolet light having a wavelength of 285 nm is in a range of 0.6 to 13.1 percent. This allows ultraviolet light reflected by the reflection portion to be used again for the sterilization. Thus, the sterilization for the fluid inside the housing can be efficiently performed. Further, a portion of ultraviolet light that has been transmitted can be detected by the light receiving unit arranged outside the housing.

The reflection portion may be polytetrafluoroethylene (PTFE) that has an amorphous crystalline structure in a portion thereof. This allows for an increase in the diffuse reflectance.

Regarding the reflection portion, the thickness may be in a range of 1 to 20 mm. The thickness is preferably 2 mm or more and 9 mm or less. This allows for both the reflection and transmission of ultraviolet light at the reflection portion.

The semiconductor light-emitting element may emit ultraviolet light whose peak light emission wavelength is in a range of 250 nm to 350 nm. This allows for an increase in sterilization effects.

The housing may have a cylindrical sterilization chamber that has the reflection portion, and an inlet port for the fluid and an outlet port for the fluid that are provided in a direction intersecting with the longitudinal direction of the sterilization chamber. The light source is arranged outside at least one of both ends of the sterilization chamber in the longitudinal direction, and the incidence portion is provided between the light source and the sterilization chamber.

Optional combinations of the aforementioned constituting elements, and implementations of the invention in the form of methods, other apparatuses, and systems may also be practiced as additional modes of the present invention.

Described below is an explanation of the embodiments of the present invention with reference to figures. In the explanation of the figures, like numerals represent like constituting elements, and duplicative explanations will be omitted appropriately. The structure described below is by way of example only and does not limit the scope of the present invention.

(Fluid Sterilization Apparatus)

FIG. 1 is a schematic diagram showing a schematic configuration of a sterilization apparatus according to the present embodiment. A sterilization apparatus 100 sterilizes bacteria, etc., included in a fluid that passes through a sterilization chamber by irradiating the sterilization chamber with ultraviolet light.

The sterilization apparatus 100 is provided with: a housing 10, which forms a flow passage through which a fluid F subject to sterilization passes; a light source 14, which has a semiconductor light-emitting element 12 that emits ultraviolet light; a light receiving unit 16, which receives a portion of the ultraviolet light emitted from the light source 14 and detects the amount of ultraviolet light that has been received; and a control unit 18, which controls the output of the semiconductor light-emitting element 12 based on information regarding the amount of ultraviolet light acquired from the light receiving unit 16. The housing 10 has an incidence portion 20 on which ultraviolet light becomes incident and a reflection portion 22, which reflects the ultraviolet light at the inner surface thereof.

The reflection portion 22 is formed of a material that transmits a portion of ultraviolet light, and the light receiving unit 16 is provided at a position where the light receiving unit 16 can receive the portion of ultraviolet light L1 that has been transmitted through the reflection portion 22. For the light receiving unit 16, a photodiode or the like is used.

The housing 10 has a cylindrical sterilization chamber 24, which has the reflection portion 22, and an inlet port 26 for the fluid F and an outlet port 28 for the fluid, which are provided in a direction intersecting with the longitudinal direction of the sterilization chamber 24. The housing 10 according to the present embodiment has a cylindrical portion 30 formed of an amorphous fluorine resin that has an amorphous crystalline structure in at least a portion thereof (for example, polytetrafluoroethylene (PTFE) that has an amorphous crystalline structure) and flange portions 32 and 34 placed respectively at openings at both ends of the cylindrical portion 30.

The cylindrical portion 30 is a member having an inner diameter of approximately 15 to 25 mm. The flange portion 32 is a component formed of PFA (tetrafluoroethylene-perfluoroalkyl vinyl ether copolymer) where an incidence portion 20 and the inlet port 26 are formed and is a member that mostly transmits ultraviolet light. In the same way, the flange portion 34 is a component formed of PFA where an incidence portion 20 and the outlet port 28 are formed. The cylindrical portion 30 and the flange portions 32 and 34 may be formed to be a single component formed of an amorphous fluorine resin by devising the processing.

Two light sources 14 according to the present embodiment are arranged outside the both ends of the sterilization chamber 24 in the longitudinal direction, and the incidence portion 20 is provided between a light source 14 and the sterilization chamber 24.

A light source 14 has a semiconductor light-emitting element 12, a substrate 36 on which the semiconductor light-emitting element 12 is mounted, and a power supplying unit 38 for supplying a driving signal to the semiconductor light-emitting element 12. The light source 14 is fixed to a light source mounting member 40 via the substrate 36 by a fastening member 42.

A semiconductor light-emitting element 12 according to the present embodiment is a light-emitting diode that emits ultraviolet light. The light-emitting diode according to the present embodiment has a substrate formed of sapphire, an AlGaN-based light-emitting layer, and a lattice mismatch buffer layer formed of AlN stacked between the substrate and the light-emitting layer. This allows for the achievement of a compact and highly-efficient sterilization apparatus. The semiconductor light-emitting element 12 according to the present embodiment preferably emits ultraviolet light whose peak light emission wavelength is in a range of 250 nm to 350 nm. For the light-emitting diode according to the present embodiment, a light-emitting diode whose peak light emission wavelength is 285 nm is used. This allows for an increase in sterilization effects.

The light source mounting member 40 is formed of, for example, a metal material such as aluminum and functions as a heat sink. The light source mounting member 40 is integrated with the flange portion 32 (or the flange portion 34) and the cylindrical portion 30 by means of the fastening member 44. On a bottom portion 40b of a recessed portion 40a where the light source 14 is mounted, a cone (polygonal pyramid) shaped through hole 40c is formed so as to face a light-emitting surface of the semiconductor light-emitting element 12. An inner surface 40d of the through hole 40c is metal mirror finished and functions as a reflector.

Therefore, since a portion of ultraviolet light emitted from the semiconductor light-emitting element 12 enters the sterilization chamber 24 from the incidence portion 20 while being reflected at the inner surface 40d, the widening of the irradiation angle of ultraviolet light entering from the incidence portion 20 can be suppressed. As a result, the ultraviolet light that has entered from the incidence portion 20 ends up irradiating a more distant position while being reflected by the reflection portion 22 of the sterilization chamber 24, and the fluid F can thus be sterilized efficiently.

In the present embodiment, a light source 14 is provided at each end of the sterilization chamber 24. Alternatively, a light source 14 may be provided only at one of the ends. In that case, a member that reflects ultraviolet light may be provided at the other end of the sterilization chamber. In FIG. 1, only the light receiving unit 16 that corresponds to the light source 14 on the left side is shown. However, a light receiving unit that corresponds to the light source 14 on the right side may be provided.

Figure 2:
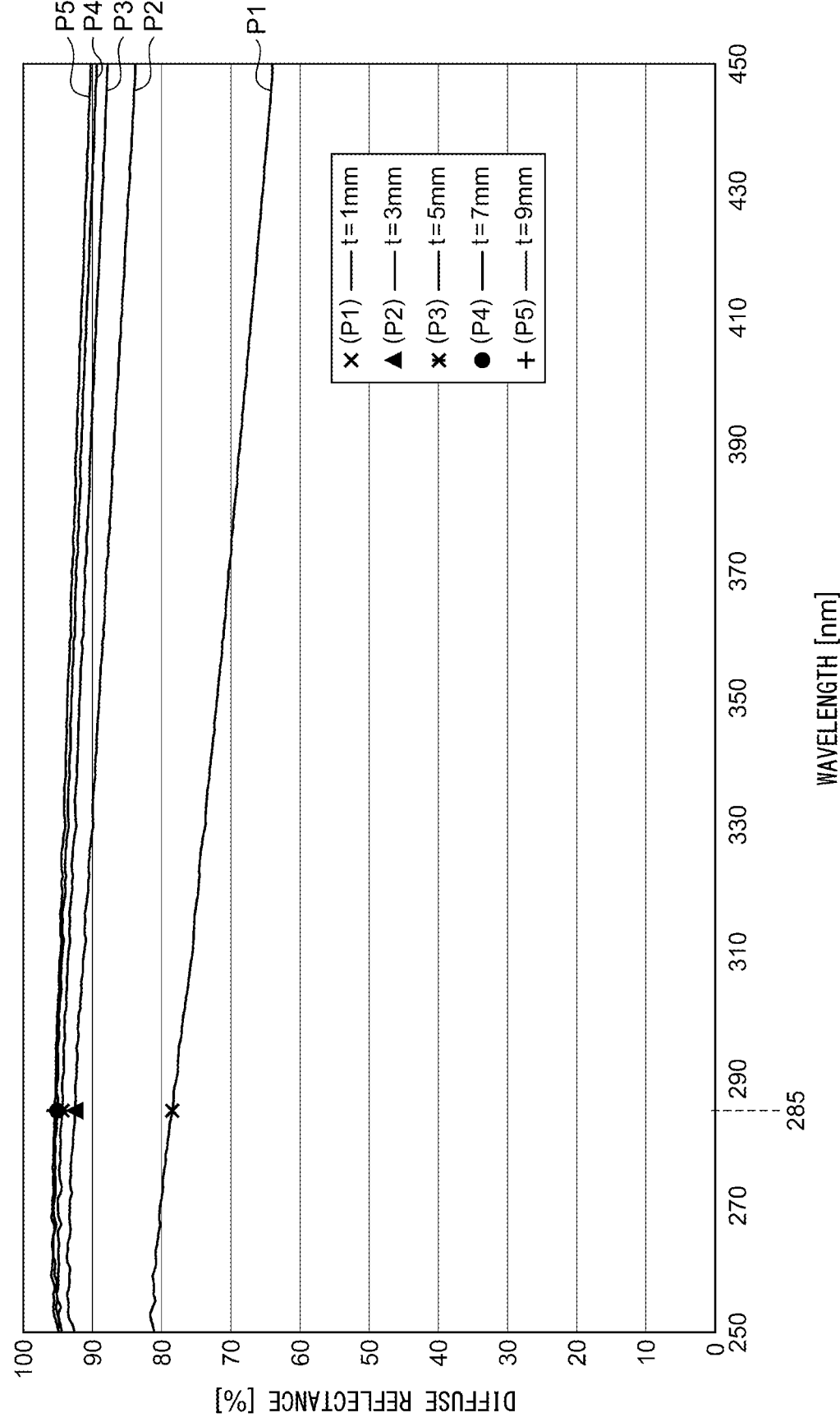
FIG. 2 is a graph showing a diffuse reflectance for each wavelength of PTFE according to the present embodiment.
Figure 3:
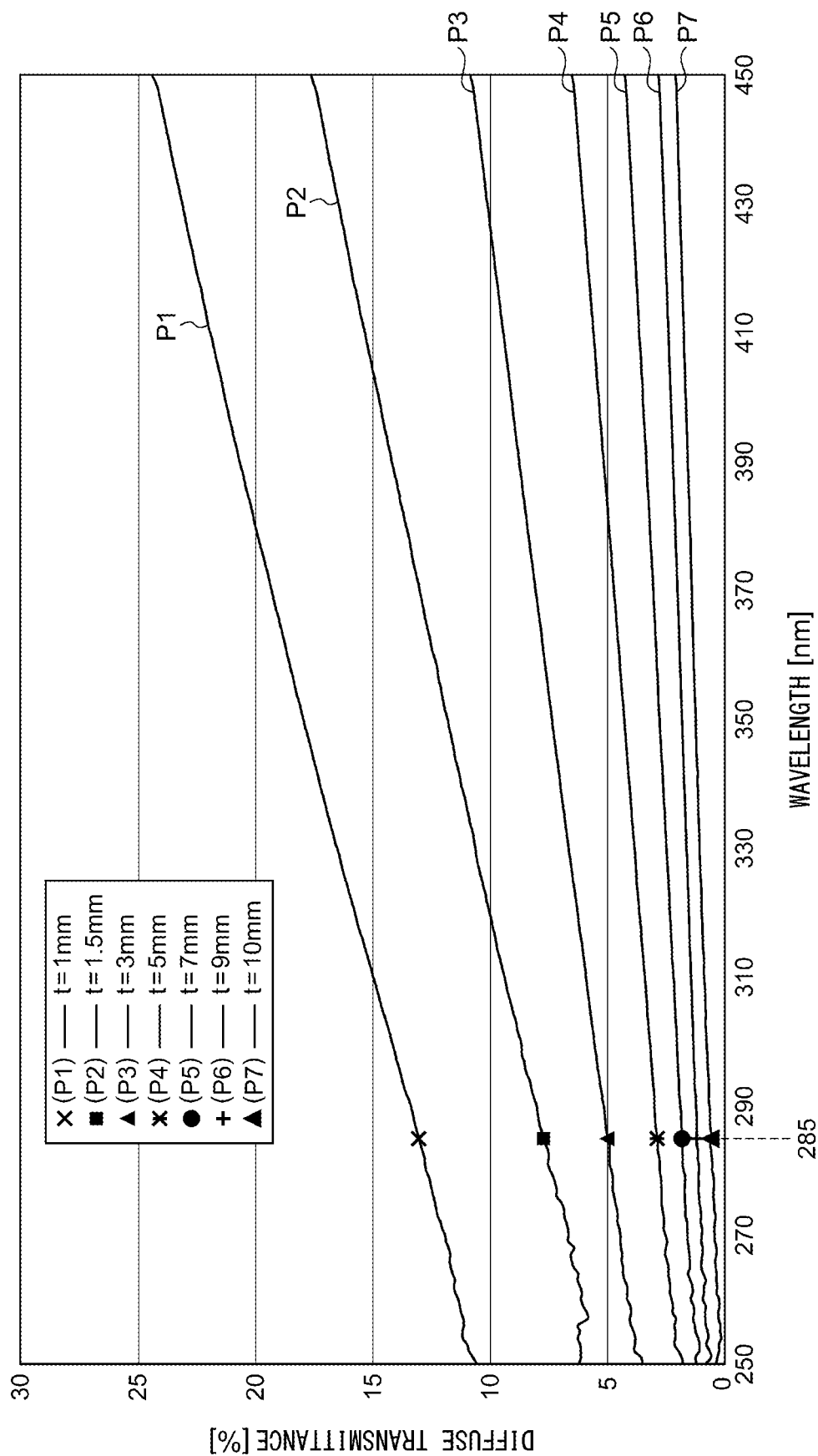
FIG. 3 is a graph showing a diffuse transmittance for each wavelength of the PTFE according to the present embodiment.

A detailed description will be made next regarding a fluorine-based resin that constitutes the cylindrical portion 30. FIG. 2 is a graph showing a diffuse reflectance for each wavelength of PTFE according to the present embodiment. FIG. 3 is a graph showing a diffuse transmittance for each wavelength of the PTFE according to the present embodiment.

The measurement of diffuse reflectances shown in FIG. 2 was performed on PTFE samples having a thickness t of 1 mm, 3 mm, 5 mm, 7 mm, and 9 mm, respectively. Three PTFE samples were prepared for each thickness, and an average value of the respective measurements of the samples was calculated and graphed.

As shown in FIG. 2, it can be found that a diffuse reflectance goes up as the thickness t becomes larger. Further, the diffuse reflectance gradually goes down toward a long wavelength side. When the semiconductor light-emitting element 12 according to the present embodiment has a peak light emission wavelength of 285 nm, the diffuse reflectance is 78.5 percent when the thickness t of PTFE is 1 mm, the diffuse reflectance is 92.5 percent when the thickness t is 3 mm, the diffuse reflectance is 94.3 percent when the thickness t is 5 mm, the diffuse reflectance is 95.1 percent when the thickness t is 7 mm, and the diffuse reflectance is 95.4 percent when the thickness t is 9 mm. As described, the diffuse reflectance for ultraviolet light can be increased by using the PTFE resin according to the present embodiment.

The measurement of diffuse transmittances shown in FIG. 3 was performed on PTFE samples having a thickness t of 1.5 mm, 3 mm, 5 mm, 7 mm, 9 mm, and 10 mm, respectively. Three PTFE samples were prepared for each thickness, and an average value of the respective measurements of the samples was calculated and graphed.

As shown in FIG. 3, it can be found that a diffuse transmittance goes down as the thickness t becomes larger. Further, the diffuse transmittance gradually goes up as the wavelength becomes longer. When the semiconductor light-emitting element 12 according to the present embodiment has a peak light emission wavelength of 285 nm, the diffuse transmittance is 13.1 percent when the thickness t of PTFE is 1 mm, the diffuse transmittance is 7.7 percent when the thickness t is 1.5 mm, the diffuse transmittance is 5.0 percent when the thickness t is 3 mm, the diffuse transmittance is 2.9 percent when the thickness t is 5 mm, the diffuse transmittance is 1.8 percent when the thickness t is 7 mm, the diffuse transmittance is 1.2 percent when the thickness t is 9 mm, and the diffuse transmittance is 0.6 percent when the thickness t is 10 mm.

As described, the PTFE that constitutes the cylindrical portion according to the present embodiment can transmit a portion of ultraviolet light while reflecting the most part of the ultraviolet light. In other words, ultraviolet light that is detected by the light receiving unit 16 of the fluid steriliza-tion apparatus 100 according to the present embodiment is a portion of ultraviolet light that has been transmitted through the reflection portion 22. Since ultraviolet light that has been transmitted through the reflection portion 22 does not contribute to the sterilization, detecting the amount of light by the light receiving unit 16 by using such ultraviolet light prevents the amount of ultraviolet light used for the sterilization from being reduced. Further, by controlling the output of the semiconductor light-emitting element 12 based on information regarding the amount of ultraviolet light acquired by the light receiving unit 16, the output of the light source can be stabilized.

Further, the light receiving unit 16 is arranged in a region opposite to the incidence portion 20 across the reflection portion 22. This allows the light receiving unit 16 to be provided outside the housing 10, thus increasing the degree of freedom for the layout designing of each component.

Regarding the reflection portion 22, the thickness can be selected, for example, in a range of 1 to 20 mm. The thickness is preferably in a range of 1 to 9 mm as described above, and the thickness is more preferably 2 mm or more and 5 mm or less. This allows for both the reflection and transmission of ultraviolet light at the reflection portion.

Further, the reflection portion 22 is preferably formed of a material whose diffuse reflectance for ultraviolet light having a wavelength of 285 nm is in a range of 78.5 to 95.4 percent and whose diffuse transmittance for ultraviolet light having a wavelength of 285 nm is in a range of 0.6 to 13.1 percent, as described above. This allows ultraviolet light reflected by the reflection portion 22 to be used again for the sterilization. Thus, the sterilization for the fluid F inside the housing 10 can be efficiently performed. Further, a portion of ultraviolet light that has been transmitted can be detected by the light receiving unit 16 arranged outside the housing 10.

While the invention has been described by referring to the above-described embodiment, the invention is not limited to the above-described embodiment, and the appropriate combination of the configurations of the embodiment or the substitution thereof is also included in the invention. Also, it is understood by those skilled in the art that various modifications such as changes in the order of combination or processing made as appropriate in each embodiment or changes in design may be added to the embodiments based on their knowledge and the embodiments added with such modifications are also within the scope of the present invention.

The invention claimed is:

1. A fluid sterilization apparatus comprising:
    a light source comprising a semiconductor light-emitting element that emits ultraviolet light;
    a housing that forms a flow passage through which a fluid subject to sterilization passes;
    a light receiving unit that receives a portion of the ultraviolet light emitted from the light source and detects the amount of ultraviolet light that has been received; and
    a control unit that performs control to stabilize the output of the semiconductor light-emitting element based on information regarding the amount of ultraviolet light acquired from the light receiving unit,
    wherein the housing has an incidence portion on which ultraviolet light becomes incident and a reflection portion that reflects the ultraviolet light at an inner surface thereof,
    wherein the reflection portion is formed of a material that transmits a portion of ultraviolet light, and wherein the light receiving unit is provided at a position where the light receiving unit receives the portion of ultraviolet light emitted from the light source that has been transmitted through the material of the reflection portion with an acute incident angle and without being reflected by the housing, wherein a diffuse reflectance of the material of the reflection portion for ultraviolet light having a wavelength of 285 nm is in a range of 78.5 to 95.4 percent and a diffuse transmittance of the material of the reflection portion for ultraviolet light having a wavelength of 285 nm is in a range of 0.6 to 13.1 percent.

2. The fluid sterilization apparatus according to claim 1, wherein the light receiving unit is arranged in a region opposite to the incidence portion across the reflection portion.

3. The fluid sterilization apparatus according to claim 1, wherein the reflection portion is polytetrafluoroethylene (PTFE) that has an amorphous crystalline structure in a portion thereof.

4. The fluid sterilization apparatus according to claim 1, wherein the reflection portion has a thickness in a range of 1 to 20 mm.

5. The fluid sterilization apparatus according to claim 1, wherein the semiconductor light-emitting element emits ultraviolet light whose peak light emission wavelength is in a range of 250 nm to 350 nm.

6. The fluid sterilization apparatus according to claim 1, wherein the housing has:

a cylindrical sterilization chamber that has the reflection portion; and an inlet port for the fluid and an outlet port for the fluid, which are provided in a direction intersecting with a longitudinal direction of the sterilization chamber, wherein the light source is arranged outside at least one of both ends of the sterilization chamber in the longitudinal direction, and wherein the incidence portion is provided between the light source and the sterilization chamber.

7. The fluid sterilization apparatus according to claim 1, wherein the control unit controls the output of the semiconductor light-emitting element based on information regarding the amount of the light such that the output of the light source is kept constant.

* * * * *